United States Patent [19]
Eykmann et al.

[11] Patent Number: 5,647,856
[45] Date of Patent: Jul. 15, 1997

[54] SYRINGE FOR THE CONTROLLED DISCHARGE OF VISCOUS MATERIALS

[75] Inventors: Rudolf Eykmann, Wehrheim; Joachim Fritze, Friedrichsdorf; Birgit Uhrig, Neu-Anspach; Dieter Schödel, Wiesbaden; Holger Burckhardt, Frankfurt am Main, all of Germany

[73] Assignee: Heraeus Kulzer GmbH, Wehrheim/Ts., Germany

[21] Appl. No.: 311,217

[22] Filed: Sep. 23, 1994

[30] Foreign Application Priority Data

Sep. 23, 1993 [DE] Germany .................. 43 32 307.3

[51] Int. Cl.⁶ ........................................ A61M 5/00
[52] U.S. Cl. ................... 604/181; 604/218; 604/235
[58] Field of Search .................... 604/181, 232–235, 604/72, 218, 207–211, 241, 221, 222, 224, 130, 131, 140, 141, 139, 151, 152, 155, 156; 433/89, 90; 222/175, 105, 256

[56] References Cited

U.S. PATENT DOCUMENTS

| | | | |
|---|---|---|---|
| 960,081 | 5/1910 | Fearon et al. | 222/256 |
| 1,704,921 | 3/1929 | Nicoll | 604/232 |
| 1,709,637 | 4/1929 | Steuer | 604/234 |
| 3,144,178 | 8/1964 | Sarnoff | 604/235 X |
| 3,581,399 | 6/1971 | Dragan . | |
| 3,900,954 | 8/1975 | Dragan . | |
| 4,173,227 | 11/1979 | Cassou et al. | 604/218 |
| 4,710,178 | 12/1987 | Leonard et al. | 604/209 |
| 4,738,379 | 4/1988 | Takasugi | 222/95 |
| 4,767,413 | 8/1988 | Haber et al. | 604/198 |
| 4,915,702 | 4/1990 | Haber | 604/198 |
| 5,454,793 | 10/1995 | Levander et al. | 604/235 |
| 5,531,709 | 7/1996 | Eykmann et al. | 604/218 |

FOREIGN PATENT DOCUMENTS

| | | |
|---|---|---|
| 7837177 | 3/1979 | Germany . |
| 4200044 | 7/1992 | Germany . |

OTHER PUBLICATIONS

*Charisma–Inlays Gewinn durch Perfektion und Ästhetik,* published by Haraeus Kulzer GmbH, (31292/D 125 sK dt./WPR 12 12 200), 6 pages.

*Primary Examiner*—Corrine M. McDermott
*Assistant Examiner*—V. Alexander
*Attorney, Agent, or Firm*—Webb Ziesenheim Bruening Logsdon Orkin & Hanson, P.C.

[57] ABSTRACT

A syringe having a bearing divided at least once in the axial direction of a threaded rod into bearing parts. The bearing parts are held at a distance from one another and at a distance from the threaded rod by at least one expanding part. The bearing parts, on their surfaces facing the threaded rod, have surfaces which can be brought by external pressure into engagement with the threaded rod against the resistance of the bearing parts.

19 Claims, 4 Drawing Sheets

5,647,856

SYRINGE FOR THE CONTROLLED DISCHARGE OF VISCOUS MATERIALS

BACKGROUND OF THE INVENTION

1. Field of the Invention

This invention relates generally to a syringe for the controlled discharge of viscous materials, and, more particularly to a syringe for the controlled discharge of dental materials.

2. Description of the Prior Art

A syringe of the prior art is described, for example, in the product information published by Heraeus Kulzer GmbH "Charisma-Inlays—Gewinn durch Perfektion und Ästhetik" [Charisma Inlays—Profit from Perfection and Appearance] (31292/D 125 sK dt./WPR 12 12 200). These syringes, which contain the viscous dental materials sold under the name "Charisma" (Charisma is a registered trademark of Heraeus Kulzer GmbH), have a cartridge filled with dental material. This cartridge has a tapered outer circumference on its discharge end, on which a cap is placed. In the end of the cartridge opposite the discharge end, a rotary piston is inserted which is in contact on one end with a sleeve-shaped stopper which, in turn, is in contact with the viscous material in the cartridge. The rotary piston is provided with a threaded portion which is guided in a bearing which is in the form of a nut. This nut is an approximately rectangular plate which has a central threaded opening. This nut is inserted into a slot in the insertion end of the cartridge, so that it is secured, with respect to the rotary piston screwed into the threaded hole, against rotation relative to the cartridge. To discharge the dental materials from the cartridge, the cap is removed from the cartridge and the rotary piston, which has a handle on its end, is twisted into the cartridge and the stopper is pushed toward the discharge end of the cartridge. To depressurize the stopper, which applies pressure to the material when the syringe is not being used, the rotary piston is twisted out of the cartridge in the opposite direction of rotation.

The syringes described above have been used successfully for years. But it has been found in handling the syringes that for very different materials, in particular materials which differ in terms of their viscosity and the amount of material to be discharged, that different advance speeds of the threaded rods may be required. This can be accomplished on one hand by means of the speed of rotation with which the rotary piston in the bearing advances as a result of its rotation or, on the other hand, the manufacturer can provide pistons with threads of different pitches which are rotated in corresponding bearing parts to achieve different advance speeds and rates of discharge.

Additional syringes for the discharge of viscous materials are disclosed, for example, in U.S. Pat. No. 3,581,399, German Application No. 42 00 044 A1, German GM 78 37 177 and U.S. Pat. No. 3,900,954. Each of these syringes and syringe system has specific features and characteristics. U.S. Pat. No. 3,581,399 discloses a syringe which has interchangeable tips or nozzles which, for example, are curved in the shape of a thin channel for controlled application of dental material to one spot on a tooth to be worked on. German Application No. 42 00 044 A1 discloses a dental cartridge for the discharge of a multi-component material for dental fillings which is inserted in a syringe controlled by a lever. This syringe has a pistol-like adapter into which the cartridge containing the dental material is inserted. German GM 78 37 177 discloses a syringe for the direct application of dental filling material in which the container which holds the filling material is designed as a collapsible capsule inserted into the cartridge. U.S. Pat. No. 3,900,954 discloses a syringe which is similar to the syringe disclosed in U.S. Pat. No. 3,581,399. A piston which has a projecting tip is inserted under some friction into a cartridge and the tip of the piston presses into a sleeve-shaped part in which the dental material is located. The small, sleeve-shaped part is attached to an end of the cartridge and simultaneously forms the discharge tip or nozzle for the material.

An object of the present invention is to provide a syringe for the discharge of a measured amount of viscous materials, in particular dental materials, which facilitates both the discharge of the viscous material from the syringe and the assembly or filling of the syringe by the manufacturer.

SUMMARY OF THE INVENTION

We have developed a syringe in which a bearing is divided at least once in the axial direction of a threaded rod into bearing parts. The bearing parts are held at some distance from one another by at least one expanding part in the radial direction of the threaded rod and at some distance from the threaded rod. The bearing parts, on their surfaces facing the threaded rod, have areas which can be brought by external pressure into engagement with the threaded rod against the resistance of the bearing parts.

As a result of the two bearing parts, which are engaged against the threaded rod by pressure on their outside surfaces, it is possible to screw the threaded rod against a stopper adjacent the viscous material to push the material out of the end of the cartridge. If large quantities of the material stored in the cartridge are to be discharged, the piston or threaded rod can be pushed into the cartridge and the user does not have to actuate any of the bearing parts. In that case, the bearing parts are held in their rest position, i.e., out of engagement with the threaded rod, so that the threaded rod can move freely in the axial direction of the cartridge. The bearing parts of the bearing are held by means of the expanding part in the radial direction away from the threaded rod and at some distance from one another, and therefore out of engagement with the threaded portion of the threaded rod. For the application of particularly high viscosity or pasty materials, the bearing parts can be pushed together for engagement with the threaded rod, and by means of a rotational movement of the rotary piston, pressure is exerted on the material so that strong forces can be applied on the dental materials with only a slight rotational motion. When the pressure is removed from the bearing parts of the divided bearing, the bearing parts are opened and the threaded portion of the threaded rod is immediately released. To completely remove the pressure from the stopper or from the material in the cartridge, the threaded rod can be pulled freely out of the bearing or the cartridge. It is also possible, if a set of cartridges is being used, to prepare one rotary piston, which is inserted into the respective special cartridge being used, and which can be removed from the cartridge after the cartridge is empty, or for storage purposes. When the rotary piston is reused, as a result of the opened or spread-apart bearing parts, the rotary piston can be advanced more rapidly until its end comes into contact with the stopper. For an easy discharge of the dental material without a major expenditure of force, the bearing parts can then be brought into engagement with the threaded portion of the threaded rod and the rotary piston rotated.

To hold the two bearing parts at some distance from one another and therefore from the threaded rod, expanding parts in the form of elastically deformable webs are used which can be held under tension against the direction in which they are pushed into engagement with the threaded rod. These expanding parts can be engaged, for example, in corresponding grooves which are formed in the body of the syringe or in the cartridge. In one simple configuration of the bearing parts, the expanding part or parts are formed on at least one of two opposite or facing surfaces of two opposite or facing bearing parts. Such expanding parts which are connected to a bearing part are then pressed, with a corresponding prestress, against a surface of the opposite bearing part so that these two bearing parts are held at a distance from one another by means of the expanding parts. In an alternative configuration of the bearing parts, the expanding part or parts of one bearing part are permanently connected to the opposite surfaces of another bearing part so that they hold the two bearing parts at some distance from one another. The syringe is preferably provided with two bearing parts which are formed on radially opposite sides of the threaded rod. In a simple design of the expanding parts or of the webs, the latter are located on the end surfaces of the bearing parts, i.e., on the sides which are oriented toward the axis of the rotary piston. This design can include short, pin-shaped extensions oriented in the compression direction of the bearing parts and running diagonally toward the threaded rod, and which are preferably engaged in corresponding grooves which correspond to the cartridge in a stationary fashion so that, flexibly held in the grooves, they can move to yield to the pressure applied to the bearing parts by the user.

Since the bearing parts must have a certain dimension in the axial direction of the rotary piston or of the threaded rod to form a sufficiently large handle surface so that the user can grip these bearing parts or handle surfaces, for a uniform mounting of each bearing part, it is useful to divide the expanding parts on each bearing part into two groups in the axial direction, which are located at some distance from one another in the axial direction and which consequently support each bearing part flexibly on the upper portion and on the lower portion.

In order to guarantee a correct engagement of the bearing parts with the threaded rod when pressure is applied externally while guaranteeing a disengagement of the bearing parts from the threaded rod, the bearing parts are guided in the radial direction so that they can move toward the threaded rod. Such guides can be designed, for example, in the form of guide grooves in which guide parts are engaged, whereby both the grooves and the guide parts can be associated with the bearing parts.

To provide an economical syringe or an economical syringe system, in one particularly advantageous configuration of the syringe, the bearing parts of the bearing are associated with an adapter part, in which the cartridge and the rotary piston can be inserted so that the threaded rod is guided between the bearing parts. In this configuration, the adapter part and the bearing parts form a unit into which different cartridges can be inserted as necessary. In this configuration, the rotary piston can be associated with either the cartridge to be inserted or the adapter part, or the rotary piston can form a separate component which can be individually introduced by means of the adapter part into a cartridge inserted in it, so that the end of the rotary piston is in contact with the stopper in the cartridge. To secure the cartridge which is inserted into the adapter part against axial displacement, the cartridge is locked in the adapter part. A simple but effective configuration of the lock can take the form of a bayonet fastener on the end of the cartridge into which the rotary piston is inserted. In this case, it is sufficient if the cartridge is guided only over a short length on its fastening end, and the rest of the cartridge projects beyond the underside of the adapter part. To guide the cartridge in the adapter part over its length, or to secure it in its position, it is advantageous to guide and support the cartridge in the adapter part on an end away from the insertion end. The cartridge is thereby sufficiently secured against lateral tipping.

In one simple structural configuration, the adapter part is closed by a ring cap on the end of the cartridge into which the rotary piston is inserted. This ring cap can be removed during the assembly of the adapter part, so that the bearing parts can be inserted into the housing of the adapter part from the end. Then the ring cap is inserted on the end. Such a ring cap can also be used to connect an adapter housing which consists of two halves. Such a design of the adapter part or of the housing of the adapter part consisting of two halves is preferred, in particular if the two halves of the shell are identical parts.

The bearing parts, the threaded rod and the parts of the adapter part are preferably manufactured from polyoxymethylene (POM).

The cartridge is preferably manufactured from polypropylene. In contrast to POM, polypropylene is relatively soft so that the cartridge can be easily inserted into the adapter part with a good fit.

In another embodiment, the stopper inserted into the cartridge as an inside stopper is one which has a membrane surface which is in contact with the end of the rotary piston. In the depressurized state, this membrane surface is prestressed opposite to the direction of forward motion of the rotary piston, i.e., the direction in which the material is discharged from the cartridge. When the desired amount of material has been discharged from the cartridge, the rotary piston is twisted back and the pressure is removed from the stopper or the membrane surface. The membrane surface then tends to return to its prestressed position, whereupon an underpressure is generated in the vicinity of the material, and the material is drawn back in from the discharge nozzle, so that no additional material exits from the discharge nozzle. In particular, in connection with the divided bearing for the support of the threaded rod, the bearing parts are released after a discharge of the material so that under the force of the expanding parts, they are disengaged from the threaded portion of the threaded rod and immediately release the threaded rod. After such a release, the piston rod is pushed back by the membrane surface.

Additional advantages and characteristics of the invention are explained in the following description of the embodiments illustrated in the accompanying drawings.

DESCRIPTION OF THE PREFERRED EMBODIMENTS

Figure 1:
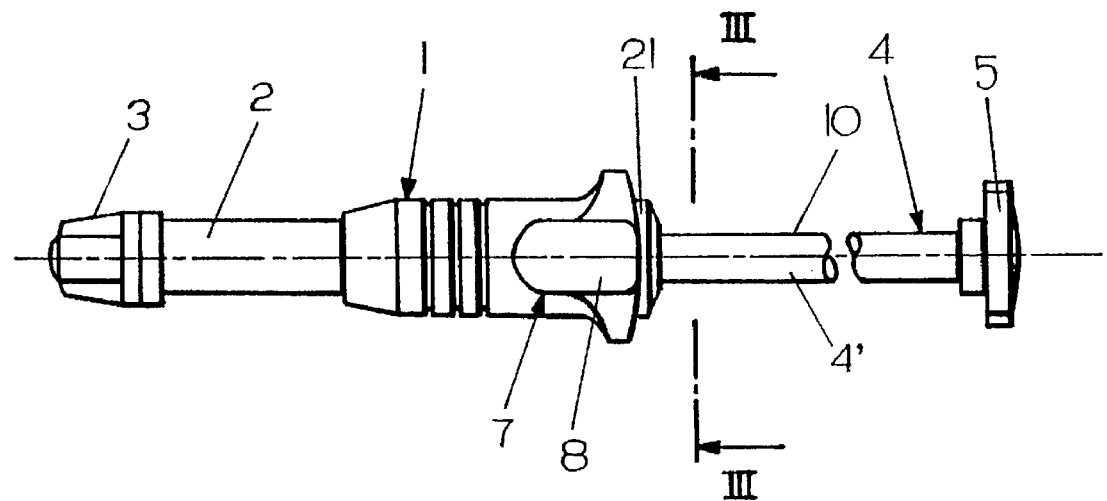
FIG. 1 shows a lateral plan view of a syringe with an adapter part and a cartridge inserted in it in accordance with the present invention.
Figure 2:
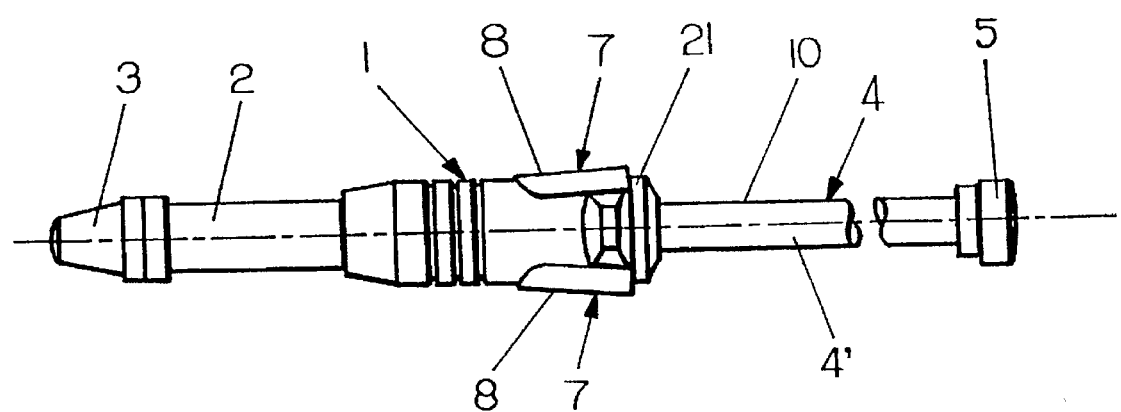
FIG. 2 shows the syringe of FIG. 1 in a view rotated 90° around a longitudinal axis.
Figure 3:
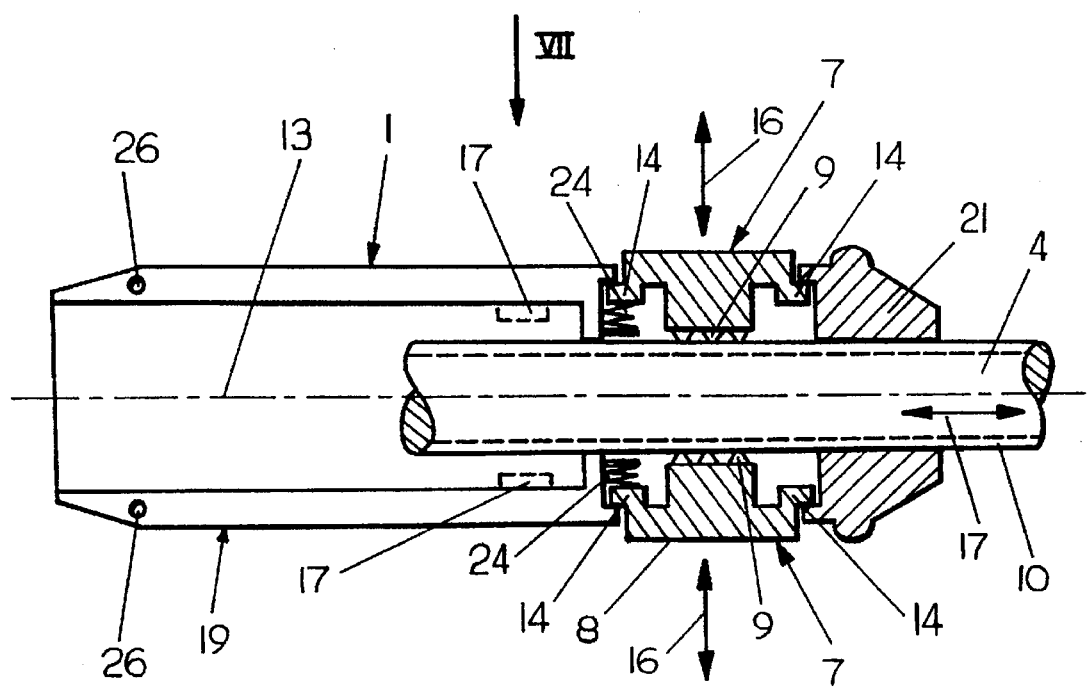
FIG. 3 shows a longitudinal section of an adapter part, similar to the embodiment illustrated in FIGS. 1 and 2.
Figure 8:
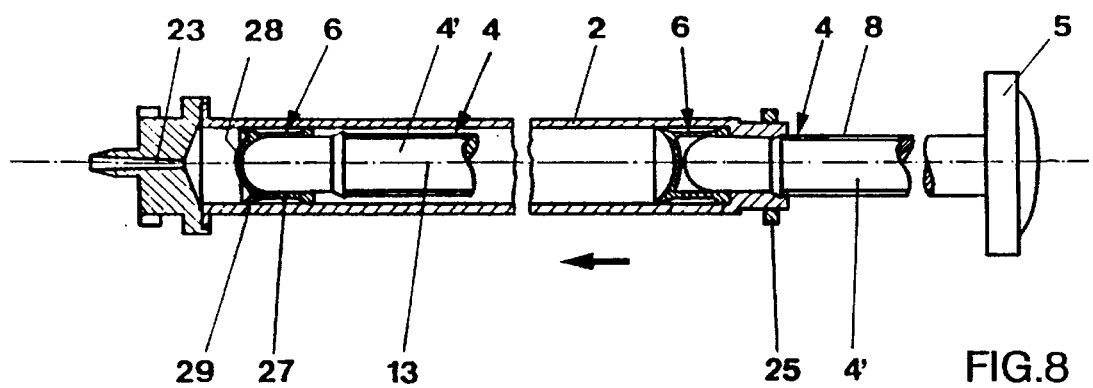
FIG. 8 is a view along the longitudinal axis of the adapter part shown in FIG. 7.
Figure 9:
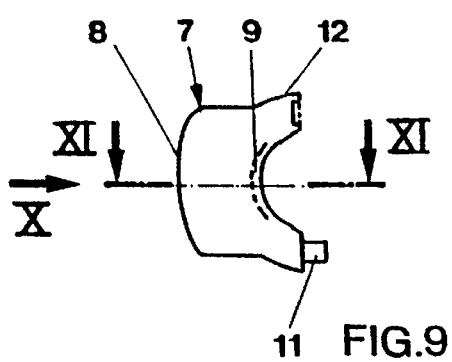
FIG. 9 is a view of an end surface of a bearing part which is inserted into the adapter part shown in FIG. 7.
Figure 10:
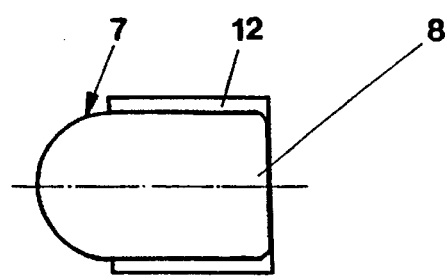
FIG. 10 is a plan view of the bearing part shown in FIG. 9, seen from the direction indicated by arrow X in FIG. 9.
Figure 11:
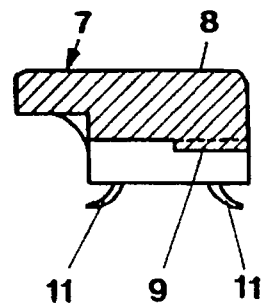
FIG. 11 is a cross section taken along lines XI—XI in FIG. 9.

The syringe for the discharge of a measured quantity of viscous materials shown in FIGS. 1 and 2 has an adapter part 1, in which a long cartridge 2 is inserted, which cartridge 2 is closed by a cap 3 on its exposed end which projects out of the adapter part 1. The cartridge 2 is filled with the material to be discharged and worked. A rotary piston 4, which is designed partly as a threaded rod 4', enters into the one end of the adapter part 1 and has a handle 5 on its exposed end. An insertion end of the rotary piston 4 presses against a stopper which is not shown in FIGS. 1 and 2 but which is visible in the embodiment shown in FIGS. 7 and 8. The threaded rod 4' of the rotary piston 4 is supported in the adapter part 1 in a bearing formed by two bearing parts 7. These bearing parts 7, as shown in FIGS. 9 to 11, each have respective handle surfaces 8 which project to a slight extent beyond the adapter part 1 and can easily be grasped by the user of the syringe. As shown in FIG. 3, on the inside of each of these bearing parts 7 is a threaded segment 9 which corresponds to the threaded portion 10 of the threaded rod 4'. Since the two bearing parts 7 face one another in the adapter part 1, as shown by way of example in FIG. 2, the threaded rod 4' is guided and centered by means of the facing threaded segments 9 of the bearing parts 7. In the starting position (when the syringe is not being used), the two bearing parts 7 are held at a radial distance from the threaded rod 4' by expanding parts in the form of elastically deformable webs 11 which are supported in corresponding grooves (not shown in detail) in the adapter part 1. Outwardly, i.e., in the radial direction from the threaded rod 4', the bearing parts 7 are held by expanded edge strips 12, as shown in FIG. 9.

To discharge pasty material from the cartridge 2 via the discharge nozzle 23 which is closed with the cap 3, the adapter part 1 is grasped by the user with one hand so that the two handle surfaces 8 of the bearing parts 7 are between the thumb and index finger. The two bearing parts 7 can then be compressed against the force exerted radially outward by the webs 11 until the respective threaded segments 9 of the bearing parts 7 are engaged with the threaded portion 10 of the threaded rod 4'. In this position, the rotary piston 4 with the handle 5 is twisted so that it can be slowly inserted into the cartridge 2. As shown in FIG. 8, the stopper 6 is thereby pressed against the material which is then discharged in a controlled manner from the discharge nozzle 23 of the cartridge 2.

After the desired quantity of material has been discharged, the bearing parts 7 are released and are pushed by the action of the webs 11 radially outward from engagement with the threaded rod 4'. Immediately upon the disengagement of the threaded segments 9 from the threaded portion 10 of the threaded rod 4', the material which is under pressure from the stopper 6 in the cartridge 2 is depressurized so that any further discharge of the material is prevented. To further depressurize the material or to remove any material which remains in the discharge opening of the cartridge 2, the threaded rod 4' can be retracted from the cartridge 2, whereupon an underpressure is generated in the cartridge 2, as a result of which the material in the discharge opening of the discharge nozzle 23 is pulled back into the cartridge 2. After the cartridge 2 is closed by means of the cap 3, the syringe can be stored until it is needed again, whereby all of the pressure which has been applied during the discharge of the material by means of the threaded rod 4' is removed from the material. The adapter part 1 is then available to hold another cartridge, which may be filled with a different material to be applied, after the used cartridge 2 has been removed from the adapter part 1. In the field of dental medicine and dental technology in particular, such a replacement of the cartridge 2 is advantageous since in the dental field, many different types and colors of materials must be used from one patient to another and from one tool to another. All that is necessary is to prepare a single adapter piece 1 into which the different cartridges 2 can be inserted. If a cartridge 2 which has already been partly emptied and into which the stopper 6 has already been pushed to a certain depth is inserted into the adapter piece 1, the rotary piston 4 can be advanced by the user, if in the initial position of the adapter part 1 it is not engaged with the threaded segments 9 of the bearing parts 7, until the end of the rotary piston 4 comes into contact with the stopper 6. Then the two bearing parts 7 are pushed together by means of the handle surfaces 8 until the threaded segments 9 are engaged with the threaded portion 10 of the threaded rod 4'. Then, by rotating the rotary piston 4 with the handle 5, an additional controlled amount of the dental material can be discharged without any major application of force.

Figure 4:
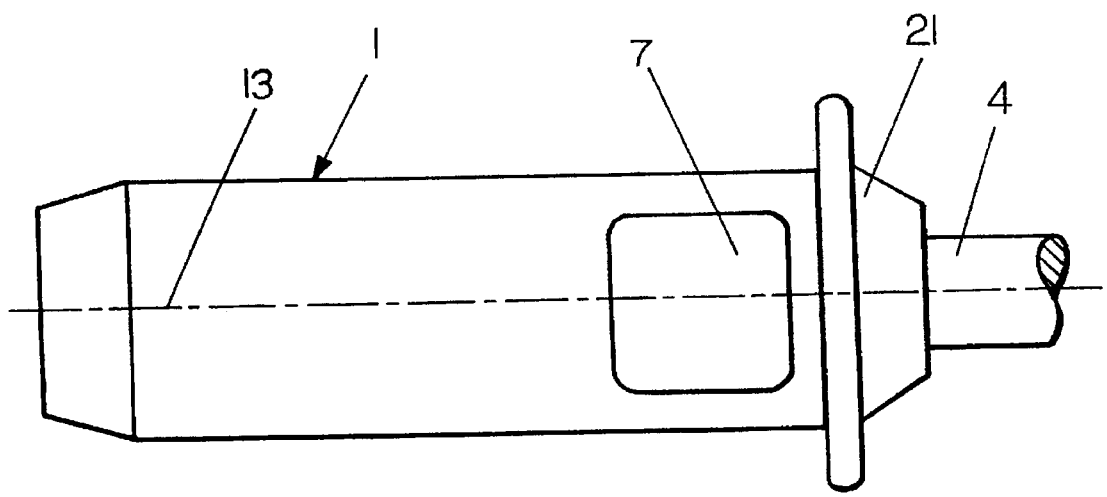
FIG. 4 is a plan view of the adapter part shown in FIG. 3, seen from the direction of arrow VII in FIG. 3.

The embodiment of the adapter part 1 shown in FIGS. 3 and 4 differs from the embodiment shown in FIGS. 1 and 2 in that the bearing parts 7 have square handle surfaces 8. In addition, the bearing parts 7 are each held in the direction of the axis 13 of the threaded rod 4' by webs 14 in the axial direction. These webs 14 are in contact with projections 17 on the housing of the adapter part 1 and can each be moved axially in the direction indicated by the double arrow 16 in FIG. 3 with respect to the threaded rod 4', toward and away from the threaded rod 4'. FIG. 3 shows the rest position of the bearing parts 7, in which their threaded segments 9 are not engaged with the threaded portion 10 of the threaded rod 4'. In this embodiment, the bearing parts 7 are held in this position by the indicated spring elements 24, for example, which are suitably braced. But web-like expanding parts can also be inserted and the use of such web-like elements is preferred. As shown, in this position the threaded rod 4' can be pushed freely into the adapter part 1 or extracted from the adapter part 1 in the direction indicated by the double arrow 17 without rotating the threaded rod 4' around its axis 13.

Figure 5:
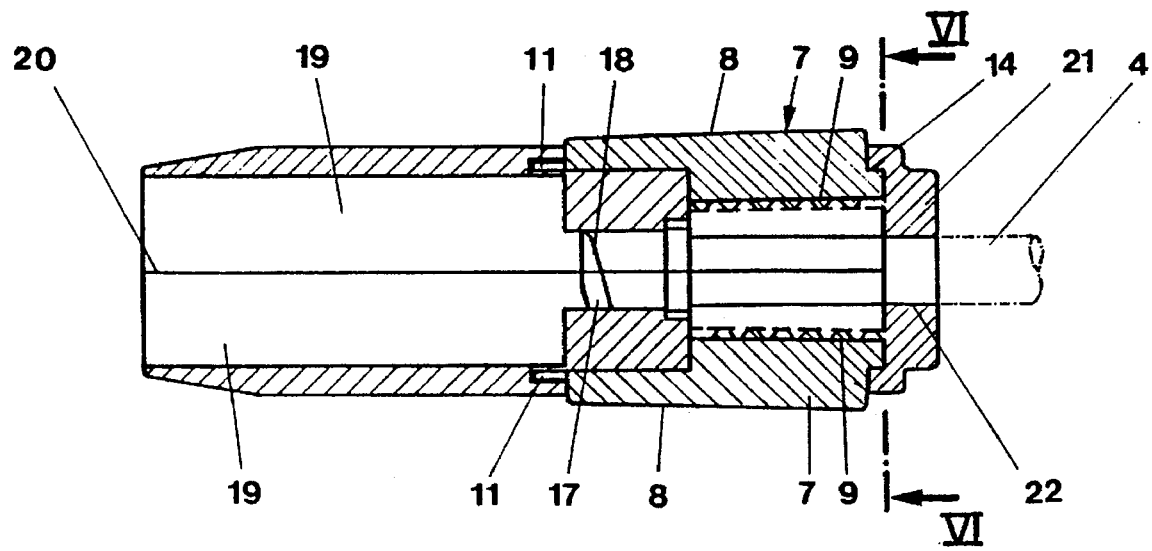
FIG. 5 is a longitudinal section of an additional embodiment of an adapter part.
Figure 7:
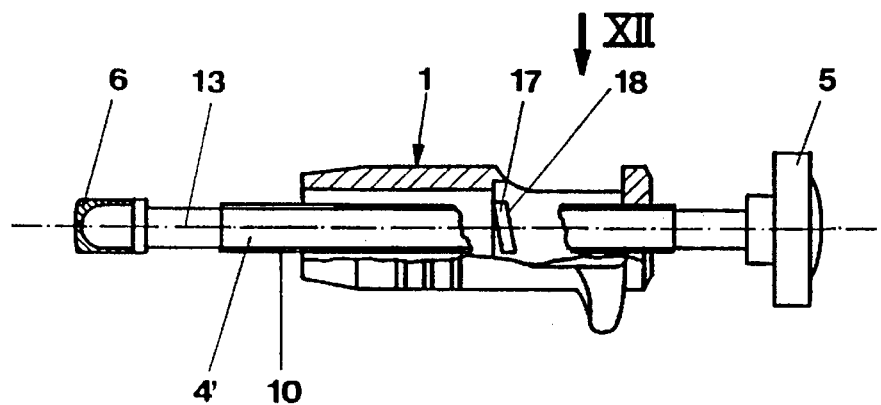
FIG. 7 is an additional embodiment of an adapter part in a partly-exploded sectional view with a rotary piston inserted.

The cartridge is removably locked in the adapter part 1 by means of a type of bayonet fastener. For this purpose, on the inner surfaces of the adapter part 1, and namely on the end away from the open side of the adapter part 1, there are projections 17 which are shown in FIGS. 3, 5 and 7 in the various embodiments of the tip. These projections 17, e.g., in the shape of short web parts, surround corresponding web parts 25 (See FIG. 8) on the end of a cartridge 2 to be inserted, whereby after the insertion of the cartridge 2 into the adapter part 1, the cartridge 2 and the adapter part 1 are rotated radially with respect to one another. To achieve a firm seating of the cartridge 2 in the adapter part 1, it is advantageous to provide the projections 17 with an oblique surface or to orient the projections 17 at an angle to a plane which stands perpendicular to the axis 13 of the threaded rod 4', whereby these diagonal surfaces of the webs surround the webs on the cartridge 2 (bayonet fastening). Such projections 17 with diagonal surfaces 18 are visible in FIGS. 3, 5 and 7.

Figure 6:
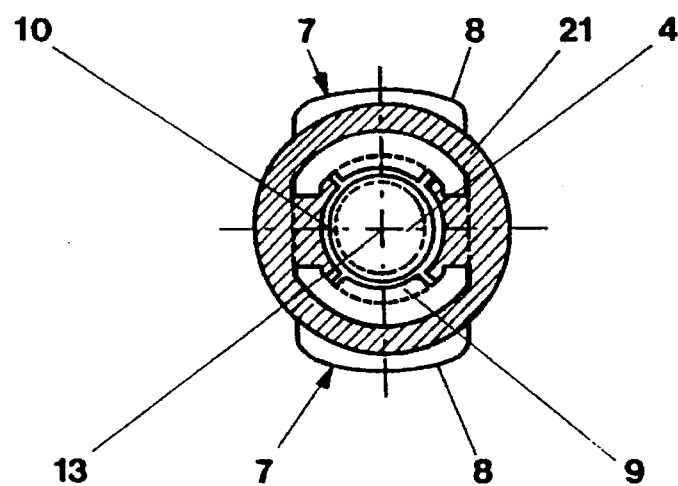
FIG. 6 is a cross section taken along lines VI—VI in FIG. 5.

In one simple design as shown in FIG. 5, the adapter part 1 is assembled from two identical shell halves 19, the surfaces of which are in contact with one another in the vicinity of the plane of separation 20, which is also the plane in which the axis 13 of the threaded rod 4' runs. On the one end, from which the cartridge 2 projects, the two shell halves 19 of the adapter part 1 are connected to one another by interlocking connecting parts 26 (See FIG. 3) and on the other end, the end where the threaded rod 4' is inserted into the adapter part 1, they are held together by means of a ring cap 21 on the end. The connecting parts 26 can be knobs which are locked in corresponding holes. The ring cap 21 encloses parts of the two shells 19, as shown in FIGS. 6 and 8. This ring cap 21 can be designed so that after it is clamped onto the shells 19, it remains there permanently. For this purpose, there can be an encircling groove on the shells 19 and/or the ring cap 21 on one hand, and an encircling web on the shells 19 or the ring cap 21 on the other hand, which are engaged with one another. The opening 22 in the ring cap 21 for the passage of the rotary piston 4 is sized so that it is only slightly larger than the outside diameter of the threaded rod 4' and in this manner forms a guide for the threaded rod 4', in particular when the two bearing parts 7 are not engaged with the threaded segment 9 on the threaded portion 10 of the threaded rod 4'. The two bearing parts 7, which are substantially identical parts, are inserted from the inside into the shells 19 during the assembly of the adapter part 1, before the application of the ring cap 21.

FIG. 8 shows a sectional view through the cartridge 2 which is inserted into the adapter part 1 shown in FIG. 7. In this cartridge 2, the stopper 6 is shown in two different positions, namely on the right after the cartridge 2 has been filled with viscous dental material, and on the left when the stopper 6 has been pushed forward by the rotary piston 4'. The stopper 6 is a cup-shaped stopper with side walls 27 and a base surface in the form of a membrane surface 28. In the rest position of the stopper, the membrane surface 28 is curved or prestressed toward the end of the rotary piston 4. When the stopper 6 is pushed forward toward the discharge nozzle 23, the end of the threaded rod 4' presses against the membrane surface 28, which matches the curvature of the end of the rotary piston 4. During movement, the stopper 6 is sealed against the inside wall of the cartridge 2 by an encircling sealing lip 29. After the desired amount of material has been discharged from the cartridge 2 via the discharge nozzle 23, the user releases the bearing parts 7 so that they are disengaged from the threaded rod 4'. In this released position, the membrane surface 28 returns to its starting position in which it is curved and prestressed toward the end of the rotary piston 4. When the membrane surface 28 swings or snaps back, even in the initial phase, an underpressure is generated in the cartridge that pulls any material which may still be in the discharge nozzle 23 back into the cartridge 2. Thus there is no oozing or dripping of the material through the nozzle. Such a rapid release of the threaded rod 4' after the end of the discharge of the material is possible precisely because of the divided bearing parts.

While embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention which is to be given the full breadth of the appended claims and all equivalents thereof.

What is claimed is:

1. A syringe for the controlled discharge of a viscous material, comprising:

a cartridge for holding the material;

an inner stopper in said cartridge;

an adapter part having radially movable bearing parts, with each bearing part having a threaded segment;

at least one expanding part; and a rotary piston, with the rotary piston having an inserted end configured to be inserted into one end of the cartridge, with the rotary piston configured substantially in the form of a threaded rod, with the inserted end of the rotary piston configured to press against the inner stopper, with the threaded rod movably held in the adapter part between the bearing parts, with the bearing parts held in a rest position by the at least one expanding part at a distance from one another in a radial direction of the threaded rod and at a distance from the threaded rod such that the threaded segments of the bearing parts are spaced from the threaded rod, and with the bearing parts movable between the rest position in which the threaded segments of the bearing parts are spaced at a distance from the threaded rod and a compressed position in which the threaded segments of the bearing parts directly engage the threads on the threaded rod by external pressure on the bearing parts.

2. A syringe as claimed in claim 1, wherein the expanding part is formed by at least one elastically deformable web.

3. A syringe as claimed in claim 2, wherein in an axial direction, there are at least two groups of expanding parts for each bearing part, located at some distance from one another.

4. A syringe as claimed in claim 1, wherein the expanding part is formed on at least two opposite surfaces of two opposite bearing parts.

5. A syringe as claimed in claim 1, wherein the expanding part is connected to an opposite surface of the bearing parts.

6. A syringe as claimed in claim 1, wherein at least two bearing parts are formed which lie on radially opposite sides of the threaded rod.

7. A syringe as claimed in claim 1, wherein the expanding part is formed on a side of the bearing parts facing the threaded rod.

8. A syringe as claimed in claim 1, wherein the expanding part is held in grooves in the syringe.

9. A syringe as claimed in claim 1, wherein the bearing parts are guided in guides so that they can move in the radial direction.

10. A syringe as claimed in claim 1, wherein the cartridge is locked in the adapter part to prevent axial displacement.

11. A syringe as claimed in claim 10, wherein the cartridge is locked by means of a bayonet fastener.

12. A syringe as claimed in claim 11, wherein one part of the bayonet fastener is located on an end of the cartridge in which the rotary piston is inserted.

13. A syringe as claimed in claim 10, wherein the cartridge can be locked in the adapter part by an axial rotation of the cartridge against a stop in a direction of rotation and advance of the rotary piston.

14. A syringe as claimed in claim 1, wherein the cartridge is guided in a guide in the adapter part on an end farther from an insertion end.

15. A syringe as claimed in claim 1, wherein the adapter part, on an end in which the threaded rod is inserted, is closed by a ring cap on an end surface through which the threaded rod passes.

16. A syringe as claimed in claim 15, wherein the adapter part is formed from two shell halves.

17. A syringe as claimed in claim 16, wherein the two shell halves are substantially identical parts.

18. A syringe as claimed in claim 1, wherein there are two bearing parts which are substantially identical.

19. A syringe as claimed in claim 1, wherein the inner stopper has a membrane surface contacting the end of the rotary piston, and wherein in a depressurized state, the membrane surface is prestressed against a direction of forward thrust of the rotary piston.

* * * * *